United States Patent

Healy et al.

[11] Patent Number: 5,298,669
[45] Date of Patent: Mar. 29, 1994

[54] PERSTRACTION SWEEP STREAM FOR A MEMBRANE REACTOR

[75] Inventors: Francis J. Healy, Florham Park; Joel R. Livingston, Basking Ridge; Edmund J. Mozeleski, Califon; John G. Stevens, Westfield, all of N.J.

[73] Assignee: Exxon Chemical Patent Inc., Linden, N.J.

[21] Appl. No.: 35,851

[22] Filed: Mar. 23, 1993

[51] Int. Cl.$^5$ .................... C07C 45/78; C07C 45/50
[52] U.S. Cl. .................... 568/492; 204/131; 204/182.4; 502/4; 568/451; 568/454
[58] Field of Search ............ 204/182.4, 131; 568/451, 454, 492; 502/404

[56] References Cited

U.S. PATENT DOCUMENTS

| | | | |
|---|---|---|---|
| 4,837,054 | 6/1989 | Schucker | 427/244 |
| 4,845,306 | 7/1989 | Puckette | 568/454 |
| 4,914,064 | 4/1990 | Schucker | 502/4 |
| 4,929,357 | 5/1990 | Schucker | 210/640 |
| 4,962,271 | 10/1990 | Black et al. | 585/819 |
| 4,976,868 | 12/1990 | Sartori et al. | 210/640 |
| 5,000,832 | 3/1991 | Steiniger et al. | 568/492 |
| 5,012,035 | 4/1991 | Sartori et al. | 585/819 |
| 5,012,036 | 4/1991 | Sartori et al. | 585/819 |
| 5,019,666 | 5/1991 | Sartori et al. | 585/819 |
| 5,039,417 | 8/1991 | Schucker | 210/640 |
| 5,039,418 | 8/1991 | Schucker | 210/640 |
| 5,039,422 | 8/1991 | Schucker | 210/651 |
| 5,049,281 | 9/1991 | Schucker | 210/640 |
| 5,063,186 | 5/1991 | Schucker | 502/4 |
| 5,075,006 | 12/1991 | Schucker | 210/500.27 |
| 5,096,592 | 3/1992 | Schucker | 210/654 |
| 5,104,532 | 4/1992 | Thompson et al. | 210/224 |
| 5,180,854 | 1/1993 | Abatjoglou et al. | 568/454 |

FOREIGN PATENT DOCUMENTS

| | | | |
|---|---|---|---|
| 0312375 | 4/1989 | European Pat. Off. | B01D 13/04 |
| 0312376 | 4/1989 | European Pat. Off. | D01D 13/00 |
| 0466469 | 1/1992 | European Pat. Off. | C07C 7/144 |

Primary Examiner—Werren B. Lone
Attorney, Agent, or Firm—J. J. Mahon

[57] ABSTRACT

A method for separating a noble metal catalyst from a crude reaction product of a noble metal-catalyzed hydroformylation reaction which comprises: (a) contacting the crude reaction product under perstraction conditions with a membrane capable of allowing a substantial portion of unreacted olefin feed and hydroformylation reaction product to pass therethrough as permeate while retaining a substantial portion of the catalyst as retentate; (b) removing the permeate by sweeping it away from the membrane by means of a sweep stream which is the same as the olefin feed used in the hydroformylation reaction; and (c) retaining the catalyst as retentate.

49 Claims, 5 Drawing Sheets

PERSTRACTION SWEEP STREAM FOR A MEMBRANE REACTOR

The present invention relates generally to the use of reactor feed as the sweep stream during membrane separation of the reaction products under perstraction conditions. This is particularly effective in the separation of noble metal catalysts from the resultant aldehydes formed by hydroformylation, whereby the olefinic feed used to form the aldehydes is also used as the sweep stream or solvent.

BACKGROUND OF THE INVENTION

Hydroformylation reactions involve the preparation of oxygenated organic compounds by the reaction of carbon monoxide and hydrogen (synthesis gas) with carbon compounds containing olefinic unsaturation. The reaction is typically performed in the presence of a carbonylation catalyst and results in the formation of compounds, for example, aldehydes, which have one or more carbon atoms in their molecular structure than the starting olefinic feedstock. By way of example, higher alcohols may be produced by hydroformylation of commercial $C_6$–$C_{12}$ olefin fractions to an aldehyde-containing oxonation product, which on hydrogenation yields the corresponding $C_7$–$C_{13}$ saturated alcohols. The crude product of the hydroformylation reaction will contain catalyst, aldehydes, alcohols, unreacted olefin feed, synthesis gas and by-products.

A variety of transition metals catalyze the hydroformylation reaction, but only cobalt and rhodium carbonyl complexes are used in commercial oxo plants. The reaction is highly exothermic; the heat release is ca 125 kJ/mol (30 kcal/mol) The position of the formyl group in the aldehyde product depends upon the olefin type, the catalyst, the solvent, and the reaction conditions. Reaction conditions have some effect and, with an unmodified cobalt catalyst, the yield of straight chain product from a linear olefin is favored by higher carbon monoxide (CO) partial pressure. In the hydroformylation of terminal olefinic hydrocarbons, the use of a catalyst containing selected complexing ligands, e.g., tertiary phosphines, results in the predominant formation of the normal isomer.

In commercial operation, the aldehyde product used as an intermediate is converted by hydrogenation to an alcohol or by aldolization and hydrogenation to a higher alcohol. The aldol-hydrogenation route is used primarily for the manufacture of 2-ethylhexanol from propylene via n-butyraldehyde.

The hydroformylation reaction is catalyzed homogeneously by carbonyls of Group VIII metals but there are significant differences in their relative activities. Roelen, using a cobalt catalyst, discovered hydroformylation in 1938. Dicobalt octacarbonyl, $Co_2(CO)_8$, which is introduced either directly or formed in situ, is the primary conventional hydroformylation catalyst precursor. Using an unmodified cobalt catalyst, the ratio of linear to branched aldehyde is relatively low.

Introduction of an organophosphine ligand to form a complex, e.g., $Co_2(CO)_6[P(n-C_4H_9)_3]_2$, significantly improves the selectivity to the straight-chain alcohol.

Recent developments of low pressure rhodium catalyst systems have been the subject of a considerable body of patent art and literature, and rhodium-triphenyl phosphine systems have been widely, and successfully, used commercially for the hydroformylation of propylene feedstocks to produce butyraldehyde.

The first commercial process to employ a rhodium-modified catalyst was developed by Union Carbide, Davy Powergas, and Johnson Matthey. In this application, the complexed rhodium catalyst is dissolved in excess ligand and the reaction is run at relatively low pressures and temperatures as compared to other processes.

A recent process commercialization has been that of Rhone-Poulenc and Ruhrchemie which produces butyraldehyde from propylene but the ligand is a sulfonated triphenylphosphine and is utilized as a water-soluble sodium salt. Turnover rates are less than in an all-organic system, but the normal to iso ratios are high and the catalyst may be separated easily from the reaction product by separation of the aqueous layer containing the catalyst and the organic layer which constitutes the product.

In the formation of linear aldehydes using a ligand-modified rhodium-catalyzed homogenous process, the reactor comprises the rhodium complex catalyst, excess triphenylphosphine and a mixture of product aldehydes and condensation by-products. The product aldehyde may be recovered from the mixture by volatilization directly from the reactor or by distillation in a subsequent step. The catalyst either remains in or is recycled to the reactor. However, the complex catalyst and triphenylphosphine ligand are slowly deactivated and eventually the spent catalyst is removed for recovery of rhodium and reconversion to the active catalyst. This process, although effective for lower molecular weight aldehyde production, is not favored for higher molecular weight aldehydes. Higher molecular weight aldehydes have higher boiling points (i.e., distillation temperatures) and catalyst deactivation is accelerated.

In some cases, such as where the products of the reaction have relatively high boiling points or where the olefin feed is not sufficiently soluble in water to permit satisfactory reaction rates, neither the process where the products are removed from the catalyst by distillation or stripping nor where the products are decanted from an aqueous catalyst solution may be utilized successfully. In such cases, it may be advantageous to utilize an aqueous medium to contain the catalyst and add a surfactant to enhance phase contacting so as to improve rate and selectivity to the desired products. This type of process is called "Phase Transfer Catalysis." However, when a surfactant is added, some carry-over of the noble metal into the organic phase at the conclusion of the process often results.

The present inventors have discovered that when olefins are satisfactorily hydroformylated in the presence of water-soluble Group VIII noble metal-ligand complex catalysts, the catalyst can be recovered quantitatively from a crude reaction product which includes the olefinic feed, aldehydes and alcohols by employing membrane separation either internal or external to the hydroformylation reactor.

A variety of membrane separation processes have also been tested for separating high boiling point products from an oil soluble catalyst complex. Attempts have been made to create large catalyst complexes which could be separated by ultrafiltration. In one case, high molecular weight phosphine ligands were used to form a homogeneous catalyst complex. High molecular weight polymeric phosphine ligands are synthesized by reacting polyvinylchloride, polychloroprene or brominated polystyrene with lithium diphenylphosphide at 20° C to 25° C. These homogeneous catalysts containing bulky ligands are thought to be more easily separated from the reaction products by ultrafiltration. See Imyanitov et al., All-Union Scientific Research Institute of Petrochemical Processes, *Neftekhimiva*, 32, No. 3:200–7 (May-June 1992). The process described herein uses a smaller catalyst complex which is not attached to a polymeric backbone.

It has been known to use membranes to separate catalysts from an aqueous solution. An example is set forth in European Patent No. 0 263 953, published on Aug. 29, 1986 (assigned to Ruhrchemie Aktiengesellschaft), which discloses a process for separating rhodium complex compounds, which contain water-soluble organic phosphines as ligands, from aqueous solutions in which excess phosphine ligand and, if necessary, other components are also dissolved, is characterized by the fact that the aqueous solution is subjected to a membrane separation process. According to this process, volatile organic substances are separated from the solution prior to conducting the membrane separation process. A typical membrane for use in this process is a cellulose acetate membrane. This process only involves the separation of water-soluble ligands and noble metal catalyst from an aqueous solution. As such, this separation process does not pertain to the separation of a water-soluble noble metal catalyst and a water-soluble ligand from an organic-aqueous emulsion, dispersion or suspension produced from a hydroformylation process.

Another patent which utilizes cellulose acetate, silicone rubber, polyolefin or polyamide membranes in the separation of catalysts from high boiling by-products of the hydroformylation reaction is Great Britain Patent No. 1312076, granted on May 15, 1970. According to this patent the aldehydes produced during the hydroformylation process are continuously withdrawn as an overhead vapor stream. The liquid stream containing the heavy by-products with the catalyst is passed over a membrane wherein approximately 78–94.3% of the catalyst is retained and the heavy by-products permeated. This is an unacceptably low level of catalyst retention which is overcome by the process of the present invention.

In like manner, Great Britain Patent No. 1432561, granted on Mar. 27, 1972, (assigned to Imperial Chemical Industries Ltd.) discloses a process for the hydroformylation of olefins which comprises reacting an olefin at elevated temperature and pressure with CO and $H_2$ in the presence of a compound of a group VIII metal and a biphyllic ligand of a trivalent P, As or Sb to give a crude liquid hydroformylation product containing an aldehyde and/or an alcohol, separating the aldehyde and/or alcohol from the crude product and leaving a liquid, bringing the liquid after separation of the Group VIII metal compound and free from aldehyde and alcohol under reverse osmosis conditions into contact with one side of a silicone rubber semi-permeable membrane in which the polymer chains have been at least partly crosslinked by gamma radiation, whereby the liquid retained by the membrane contains a higher concentration of Group VIII metal compounds and/or biphyllic ligand than the original liquid.

In an article by Gosser et al., entitled "Reverse Osmosis in Homogeneous Catalysis," *Journal of Molecular Catalysis*, Vol. 2 (1977), pp. 253–263, a selectively permeable polyimide membrane was used to separate soluble transition metal complexes from reaction mixtures by reverse osmosis. For example, separation of cobalt and rhodium complexes from hydroformylation products of 1-pentene. That is, a solution of 0.50 grams of $RhH(CO)(PPh_3)_3$ in 40 ml of benzene and 10 ml of 1-pentene was stirred at 50° C. with a $CO/H_2$ mixture at ca. 4 atm pressure until no further pressure drop occurred. The pentene was completely converted to aldehydes according to proton nuclear magnetic resonance (nmr) analysis. The solution was permeated through a polyimide membrane under 68 atm nitrogen pressure. The permeate (4.5 grams passed in 2 min.) showed only 9% of the original rhodium concentration by X-ray fluorescence.

The permeation rate of rhodium as set forth above, i.e., 9%, is considered unacceptable. The rhodium catalyst should be retained in an amount of greater than 99% to be a commercially feasible process.

Another example of the use of membranes to separate metal catalysts from hydroformylation products is set forth in Dutch Patent No. 8700881, published on Nov. 1, 1988. The method disclosed therein relates to one which improves the efficiency of membrane separation of hydroformylation products from expensive organometallic catalyst containing reaction mixtures. In Dutch Patent No. 8700881 a polydimethylsiloxane membrane having a thickness of 7 microns applied to a Teflon ® support was used in the separation of a reaction mixture containing $C_9$-$C_{15}$ alcohols, a homogeneous catalyst system comprising an organometallic complex of a transition metal from Group VIII or VIIa or Va of the Periodic Table, e.g., a tricarbonyl (triphenyl-phosphine) cobalt catalyst, and 40% low-viscosity lubricating oil (an antiswelling or de-swelling agent). At a flow of 133 kg/$m^2$-day, the cobalt contents in the feed, retentate, and permeate were 600, 910, and 18 ppm, verses 840, 1930, and 160 ppm, respectively, for a mixture without the de-swelling agent. This process is directed to the separation of product from a reaction mixture containing a homogeneous catalyst system by means of a membrane. The ligands disclosed in Dutch Patent No. 8700881 are all organic soluble ligands, e.g., triphenylphosphine, tri-n-alkylphosphine or acetyl acetonate. Critical to the process of Dutch Patent No. 8700881 is the addition of a de-swelling agent to the reaction mixture which assists in the separation of the products from the reaction mixture.

Each of the aforementioned processes for removing metal catalysts from crude hydroformylation reaction products are both costly in terms of unrecovered catalyst and, as such, would require further expensive treatment of the streams to recover catalyst.

The present inventors have been examining whether rhodium separation from hydroformylation products can be performed with a membrane when the catalyst complexes are formed using hydrocarbon or oil soluble phosphine ligands in the presence of an atmospheric mixture of CO and $H_2$ and also whether such a separation can be effected using water-soluble phosphine ligands at higher than atmospheric pressures of CO and $H_2$. For the organic-soluble system, they have discovered that alkylated phosphine ligands together with dense nonpolar polymeric membranes are capable of substantially retarding the rhodium loss during the separation of the rhodium catalyst from the hydroformylation reaction products. It was also discovered that triphenylphosphine ligands used in conjunction with a dense polymeric, nonpolar membrane also substantially retards rhodium catalyst loss, although not as well as alkylated phosphines. Optimum operating conditions for the organic-soluble system involve performing the separations in an atmosphere of CO and $H_2$ each with partial pressures less than one atmosphere.

For the water-soluble system the present inventors have discovered that rhodium catalysts may be separated from the reaction products using a variety of ligands and a variety of hydrophobic membranes.

In processes which produce high molecular weight products, it may not be possible to provide the driving force needed to drive the products through the membrane by pervaporation due to the need for high temperatures and high vacuum and thus perstraction would be desirable.

Perstraction typically involves the selective dissolution of particular components contained in a mixture into the membrane, the diffusion of those components through the membrane and the removal of the diffused components from the downstream side of the membrane by use of a liquid sweep stream.

For example, in perstractive separations of aromatics from saturates in petroleum or chemical streams (particularly heavy cat naphtha streams) the aromatic molecules present in the feedstream dissolve into the membrane film due to similarities between the membrane solubility parameter and those of the aromatic species in the feed. The aromatics then permeate (diffuse) through the membrane and are swept away by a sweep liquid which is low in aromatic content. This keeps the concentration of aromatics at the permeate side of the membrane film low and maintains the concentration gradient which is responsible for the permeation of the aromatics through the membrane.

The sweep liquid should be low in aromatic content so as not to itself decrease the concentration gradient. The sweep liquid is preferably a saturated hydrocarbon liquid with a boiling point much lower or much higher than that of the permeated aromatics. This is to facilitate separation, as by simple distillation. Suitable sweep liquids are $C_3$ to $C_6$ saturated hydrocarbons and lube basestocks ($C_{15}$-$C_{20}$).

The perstraction process is run at any convenient temperature, preferably as low as possible.

The choice of pressure is not critical since the perstraction process is not dependent on pressure, but on the ability of the aromatic components in the feed to dissolve into and migrate through the membrane under a concentration driving force. Consequently, any convenient pressure may be employed, the lower the better to avoid undesirable compaction, if the membrane is supported on a porous backing, or rupture of the membrane, if it is not.

If $C_3$ or $C_4$ sweep liquids are used at 25° C. or above in liquid state, the pressure must be increased to keep them in the liquid phase.

A disadvantage of conventional perstraction methods, however, is the need to provide a step to remove the perstraction sweep stream that has permeated (diffused) to the reaction side from the permeate side of the membrane.

The present inventors have developed a method which overcomes the problems associated with diffusion of the sweep stream and contamination of the reactants and products located on the reactor side of the membrane. This method uses the hydroformylation feedstock, e.g., olefins, as the sweep stream. Thus, it is also possible that the hydroformylation feed may be supplied to the reactor, in addition to the conventional feed method, by diffusion of the sweep stream through the membrane such that it is delivered to the hydroformylation reactor together with the retentate recycled to the reactor after contacting the membrane separator.

The present invention also provides many additional advantages which shall become apparent as described below.

SUMMARY OF THE INVENTION

A method for separating products from reactants in a membrane reactor which comprises a retentate compartment and a permeate compartment divided by a membrane, wherein the separation occurs under perstraction conditions and the sweep stream which passes through the permeate compartment is the same as the reactant feedstock.

This method is particularly suitable for separating a noble metal catalyst from a crude reaction product of a noble metal-catalyzed hydroformylation reaction under perstraction conditions. The method includes the steps of (a) contacting a crude reaction product under perstraction conditions with a membrane capable of allowing a substantial portion of unreacted olefin feed and hydroformylation reaction product to pass therethrough as permeate while retaining a substantial portion of the catalyst as retentate; (b) removing the permeate by sweeping it away from the membrane by means of an olefinic sweep stream which is the same as the olefinic feed used in the hydroformylation reaction; and (c) retaining the catalyst as retentate.

In accordance with another embodiment, the sweep stream permeates through the membrane so as to have the dual function of acting as both the perstraction sweep stream and a supplemental olefinic feed to the hydroformylation reactor.

Additionally, the present invention pertains to a method for producing higher aldehydes and higher alcohols which comprises: (a) hydroformylating an olefin feed with synthesis gas in the presence of a Group VIII noble metal-ligand complex catalyst to form a crude reaction product comprised of unreacted olefin feed, hydroformylation reaction product and a catalyst; (b) removing the catalyst from the crude reaction product by feeding the crude reaction product under perstraction conditions to a membrane separator which comprises a membrane capable of allowing a substantial portion of the hydroformylation reaction product and olefin feed to pass therethrough as permeate while retaining a substantial portion of the catalyst as permeate; (c) recovering the permeate by sweeping it away from the membrane by means of an olefinic sweep stream which is the same as the olefinic feed used in the hydroformylation reaction; (d) retaining the catalyst as retentate; and (e) recycling the catalyst to hydroformylation step (a).

This invention is useful in the separation of a rhodium-ligand complex catalyst from both organic and aqueous feed mediums. The ligands and membranes must be modified depending which medium is being delivered to the membrane reactor unit. The processes for treating an organic reaction medium are described above; whereas the processes for treating an aqueous reaction medium is described below.

A method for separating a water-soluble noble metal catalyst from a crude reaction product of a noble metal-catalyzed hydroformylation reaction run in aqueous solution, in an aqueous emulsion or as an aqueous suspension, the crude reaction product including an aqueous phase containing a water-soluble Group VIII noble metal-ligand complex catalyst and an organic phase containing unreacted olefin feed and an organic hydroformylation reaction product, which comprises: (a) contacting the crude reaction product under perstraction conditions with a hydrophobic membrane capable of allowing a substantial portion of the unreacted olefin feed and the organic hydroformylation reaction product to pass therethrough as permeate while retaining a substantial portion of the water-soluble Group VIII noble metal-ligand complex catalyst as retentate; (b) removing the permeate by sweeping it away from the membrane by means of a sweep stream which is the same as the olefin feed used in the hydroformylation reaction; and (c) retaining the water-soluble Group VIII noble metal-ligand complex catalyst as retentate.

Other and further objects, advantages and features of the present invention will be understood by reference to the following specification in conjunction with the annexed drawings, wherein like parts have been given like numbers.

DESCRIPTION OF THE PREFERRED EMBODIMENTS

Hydroformylation is a process for converting olefins to a product of one or more additional carbon numbers by the addition of carbon monoxide and hydrogen to the double bond(s) of the olefin in the presence of a catalyst at elevated temperatures and pressures. A typical hydroformylation process is demonstrated below:

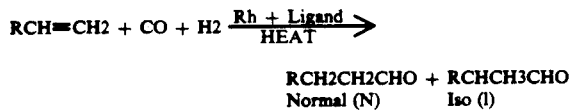

At a temperature of 100° C. and a pressure of $1.03 \times 10^6$ N/m² (150 psi) the normal to iso ratio using rhodium as the catalyst may be below 1 or even as high as 100, depending on the ligand, ratio of ligand to rhodium, etc. When cobalt is used as the catalyst and is not modified by a ligand, the normal to iso ratio is at most below 3.

Another method for catalytic hydroformylation of olefins, using a conventional approach is set forth in U.S. Pat. No. 4,399,312 (Russell et al.), which issued on Aug. 16, 1983. The hydroformylation method discussed in the above-mentioned patent involves the reacting together, at elevated temperature and pressure, of an olefin, $H_2$ and CO in the presence of a catalyst comprising a water-soluble complex of a noble metal and an amphiphilic reactant in a reaction medium comprising an aqueous phase and an organic phase. The organic phase includes a highly reactive olefin, e.g., $C_3$–$C_{20}$, and a solvent. The noble metal catalyst is typically Pt, Rh, Ru or Pd. The aqueous phase preferably contains a water-soluble phosphine in complex combination with a complex or catalytic precursor of the noble metal, e.g., sulfonated or carboxylated triaryl phosphines. The amphiphilic reagent is typically an anionic, nonionic or cationic surfactant or phase transfer agent such as a complex ammonium salt or a polyoxyethylene nonionic surfactant. The preferred ratio of aqueous phase to organic phase is 0.33:1 to 5:1, the ratio of $H_2$ to CO is 1:1 to 5:1, the content of precious metal in the aqueous phase is 100–500 ppm and the ratio of amphiphilic reagent to precious metal is up to 100:1 on a molar basis. It is preferable that the reaction be carried out at 300–10,000 kPa, especially 300–3,000 kPa and at a temperature in the range between about 40°–150° C.

Figure 1:
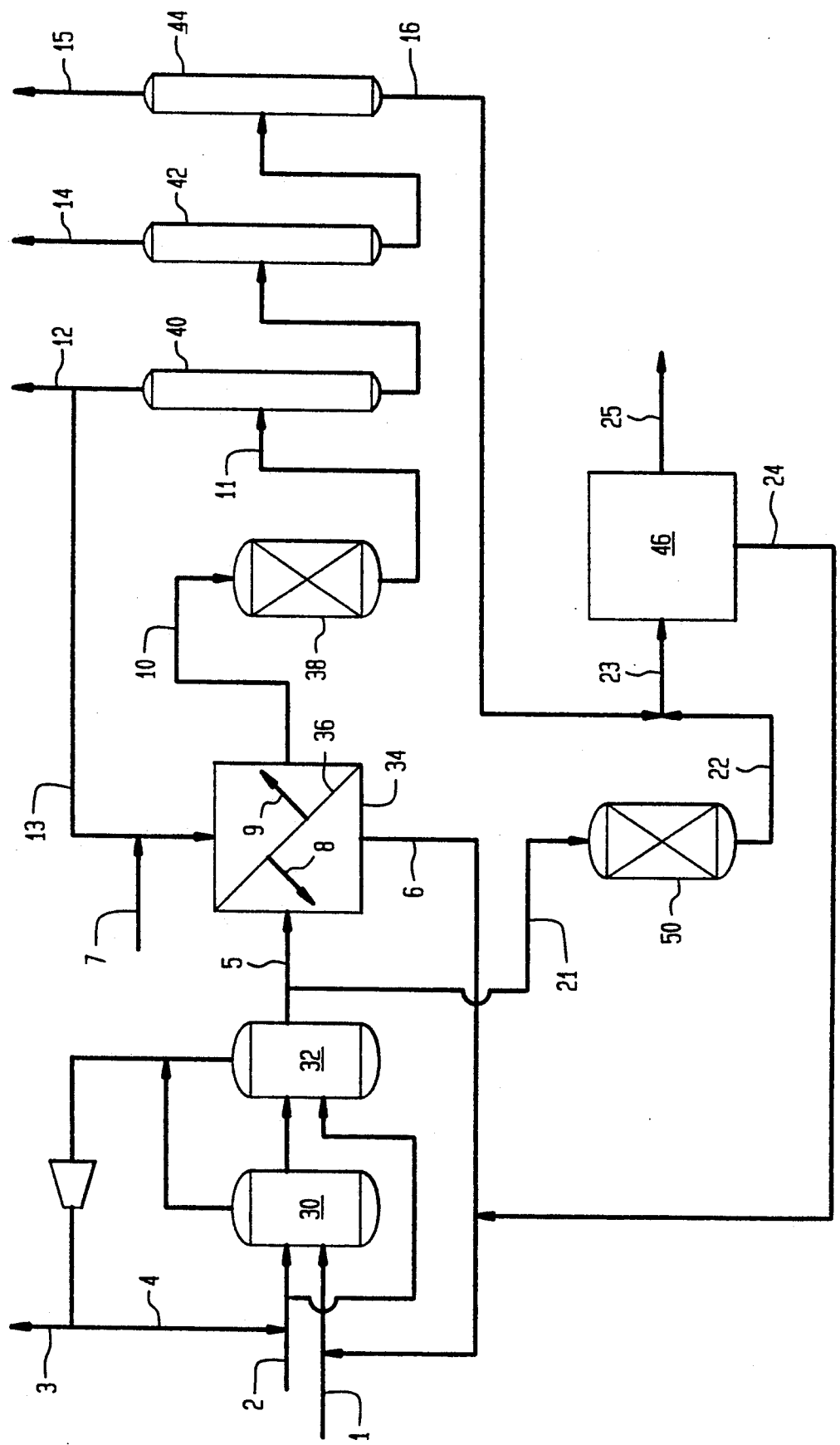
FIG. 1 is a schematic representation of a hydroformylation process wherein a reaction product is separated from an organic-soluble noble metal complex catalyst under perstraction conditions according to the present invention.

The novel method according to the present invention used for producing higher aldehydes and higher alcohols by means of hydroformylation using an organic-soluble ligand and catalyst can best be described by referring to FIG. 1. This method includes the hydroformylating of an olefin feed supplied via stream 1 and/or stream 6 together with synthesis gas which is supplied via stream 2 in the presence of a Group VIII noble metal-ligand complex catalyst within reactors 30 and 32 to form a crude reaction product comprised of unreacted olefin feed, hydroformylation reaction product and a Group VIII noble metal-ligand complex catalyst. The crude reaction product is delivered from reactors 30 and 32 via stream 5 to membrane separator 34 wherein the Group VIII noble metal-ligand complex catalyst is separated from the crude reaction product by contacting the crude reaction product under perstraction conditions against membrane 36 which is capable of allowing a substantial portion of the hydroformylation reaction product and unreacted olefin feed disposed in retentate compartment 8 to diffuse through membrane 36 into permeate compartment 9 as permeate while retaining a substantial portion of the Group VIII noble metal-ligand complex catalyst in retentate compartment 8 as retentate. The permeate in permeate compartment 9 is sweep away from membrane 36 by means of a perstraction sweep stream of olefin feed which is supplied via fresh olefin feed stream 7 and/or recycled olefin feed stream 13. Thereafter, the retentate, e.g., Group VIII noble metal-ligand complex catalyst, is recycled via stream 6 to hydroformylation reactors 30 and 32.

The permeate swept away by the sweep streams supplied by stream 7 and/or stream 13 is delivered to a secondary catalyst recovery unit 38 via stream 10. The bottoms from secondary catalyst recovery unit 38 are then passed on to a series of fractionation columns (40, 42 and 44). Fractionation column 40 takes overhead unreacted olefin which can be recycled as a perstraction sweep stream via stream 13 or purged via stream 12. The bottoms of fractionation column 40 are sent to fractionation column 42 which takes light aldehydes out overhead via stream 14. The bottoms of fractionation column 42 are sent to fractionation column 44 which takes heavy aldehydes out overhead via stream 15. The bottoms from fractionation column 44 are sent to a phosphine recovery unit 46 via streams 16 and 23 wherein heavies are removed via stream 25 and phosphines are recovered and returned to hydroformylation reactors 30 and 32 via stream 24 and stream 6. The reactor purge from hydroformylation reactor 32 is delivered via stream 21 to a secondary-type catalyst recovery unit 50 and the recovery unit effluent is sent to the phosphine recovery unit 46 via streams 22 and 23.

The noble metal-catalyzed hydroformylation reaction includes the steps of: reacting an olefin feed with hydrogen and carbon monoxide in the presence of a Group VIII noble metal-ligand complex catalyst, at a temperature in the range between about 80° to 125° C. to produce an aldehyde having a normal to iso ratio in the range between about 0.5:1 to about 80:1.

When an organic reaction medium is treated as discussed in FIG. 1, it is preferable that the ligand be an alkylated or arylated ligand, such as a $C_2$ to $C_8$ phosphine ligand with at least one alkyl group bonded to the para position. The ligand is preferably selected from the group consisting of: triphenylphosphine, para alkylated triphenylphosphines such as tri-4-tolyl phosphine, tri-4-propylphenyl phosphine and tri-4-octylphenyl phosphine, and trioctylphosphine.

The membrane which is most suitable for separating organic reaction medium is a nonpolar dense polymeric membrane such as that selected from the group consisting of: high density polyethylene radiation-crosslinked membranes, low density polyethylene radiation-crosslinked membranes, and polypropylene membranes.

The membrane is one which is capable of retaining at least about 99% of the Group VII noble metal-ligand complex catalyst.

The olefin feed is typically a $C_4$-$C_{20}$ olefin. The sweep stream can diffuse through the membrane into the retentate compartment. When the sweep stream diffuses through the membrane it can act in a dual capacity, i.e., as a perstraction sweep stream and as a reactant feedstock in the hydroformylation reaction process.

Figure 2:
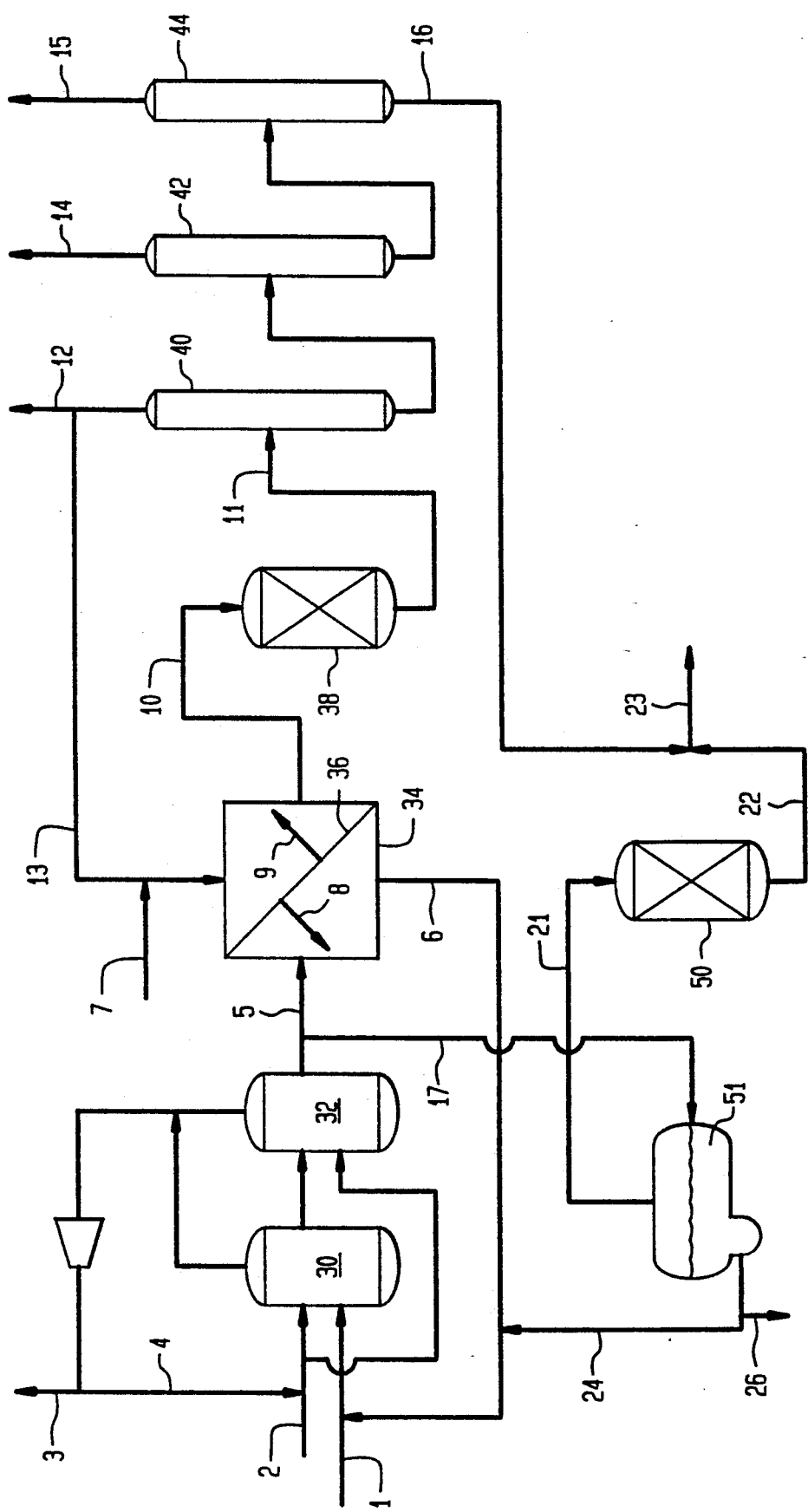
FIG. 2 is a schematic representation of a hydroformylation process wherein a reaction product is separated from an water-soluble noble metal complex catalyst under perstraction conditions according to the present invention.

FIG. 2 demonstrates the preferred process for separating water-soluble noble metal catalyst from an aqueous reaction medium. This system is similar to that described above in FIG. 1 for organic reaction mediums, except that the reactor purge from hydroformylation reactor 32 is delivered via stream 17 to a settler 51 where the aqueous stream 24 of settled reactor purge is recycled via streams 24 and 6 to hydroformylation reactors 30 and 32, or may alternately be purged or reconstituted via stream 26. The organic layer from settler 51 is sent via stream 21 to a secondary-type catalyst recovery unit 50 and the recovery unit effluent is sent via streams 22 and 23 to purge.

When treating an aqueous reaction medium it is preferable to use a ligand selected from the group consisting of Na-p-(diphenylphosphino) benzoate, Na-p-(diphenylphosphino) benzenesulfonate, Na-m-(diphenylphosphino) benzenesulfonate, and tris-(sodium m-sulfophenyl)-phosphine. In most instances it is desirable to add a surfactant to the noble metal-catalyzed hydroformylation reaction. The surfactant is preferably one compound selected from the group consisting of: cetyl trimethylammonium bromide, sodium laurate, sodium stearate, sodium p-toluenesulfonate and dodecylbenzene sulfonate.

The preferred membranes are high density polyethylene crosslinked membranes, natural latex rubber membranes, polychlorotrifluoroethylene membranes, crosslinked bromobutyl rubber membranes, and crosslinked copolymer membranes of isobutylene and p-bromomethyl styrene. One preferred membrane is a copolymer of isobutylene and p-bromomethyl styrene crosslinked with hexamethylene diamine.

The comparative examples below and in FIG. 2 demonstrate the effectiveness of using the hydroformylation reaction feed as the perstraction sweep stream during the separation of the catalyst from the aldehyde products of the hydroformylation process.

Example 1

For this example, the present inventors have conducted two comparative demonstration runs to illustrate that the olefinic feedstock can be successfully used as the perstraction sweep solvent during membrane separation of hydroformylation reaction products and unreacted olefins from a noble metal catalyst without substantially reducing the rate of permeation of the hydroformylation reaction products through the membrane. It also shows that the diffusion of the sweep solvent through the membrane to the retentate side of the membrane does not result in the contamination of the crude reaction products but does provide an effective source of feed for reaction with the catalyst to desired reaction products. These runs were conducted in an aqueous emulsion using a water-soluble phosphine ligand, e.g., sodium p-diphenylphosphino benzoic acid. The decene-1 was hydroformylated in a stirred autoclave before transfer to the membrane separator.

2 grams of lauric acid, as surfactant, were added to an aqueous solution of sodium p-diphenyl phosphino benzoate ($Ph_2P(p-C_6H_4COO_3Na)$), dissolved at approximately 70° C. with stirring under nitrogen in 70 grams of 1N $NaHCO_3$ solution. The resulting clear solution was then introduced through a Hoke bomb to a 1 liter autoclave. To this solution, a mixture of 179.23 grams of 1-decene, 9.93 grams of hexadecane as an internal standard, 1.24E-01 grams of rhodium acetate dimer (i.e., $RhII_2(OOCCH_3)_4$ dimer) and 10 grams of i-PrOH as co-solvent were introduced through the Hoke bomb under a carbon monoxide/hydrogen pressure.

The autoclave was pressurized with a mixture of $CO/H_2$ in a ratio of 1:1 and at a pressure of $6.89 \times 10^5$ $N/m^2$ (100 psig) at room temperature. The contents were then heated to 80° C. while the pressure was maintained at $1.03 \times 10^6$ $N/m^2$ (150 psig). The reaction was monitored by periodic gas chromatographic (GC) analysis of the organic layer. At the conclusion of the run the mixture was cooled and removed from the autoclave. After settling, the layers were separated and the substantially organic layer transferred to the membrane separator.

A crosslinked copolymer of isobutylene and p-bromomethyl styrene was chosen as the membrane for this experiment since it was hydrocarbon, hydrophobic, easily crosslinked and capable of meeting our stability criteria. The membrane for evaluation in the membrane separator was prepared as follows. Into a 250 ml wide mouth jar equipped with a magnetic stirring bar were added 34.17 grams of a copolymer of isobutylene and p-bromomethyl styrene plus 104.13 grams of toluene. The 25% solution was stirred magnetically until all the polymer dissolved. After stirring two days, with occasional warming to about 50° C., the polymer dissolved completely resulting in a clear yellow viscous liquid. An aliquot or 49.2 grams of the 25% polymer solution containing 12.3 grams of polymer which contained 2.2% bromine was transferred to a 100 ml wide mouth jar. To this solution was added 0.49 grams (0.0042297 m) of 1,6-hexane diamine dissolved in about 0.6 grams of toluene. After thorough hand mixing, the clear viscous yellow liquid was transferred to a centrifuge tube and centrifuged for 20 minutes at 10,000 rpm. Thereafter, three membranes were cast on Teflon ® sheets (22.86×22.86 cm) having a thickness of about 2.2 ml, a pore size of about 0.2 microns and a porosity of about 80%. The cast membranes were allowed to weather overnight in a nitrogen purge box then heated for 2 hours at 125° C. The cast membranes were examined for weight loss by extraction with refluxing cyclohexane.

The cast membrane was then mounted in the membrane reactor unit between two 100 mesh stainless steel screens. The polymer thickness was 48.5 microns, with two 53.3 micron sheets of Teflon ® on the outer surface. To the evacuated catalyst side of the membrane reactor unit was added the organic reactor product which comprised 216.4 grams (1.271 mole) of undecyl aldehdes, 16.68 grams (0.12 mole) of decenes and 14.3 grams of hexadecane as an internal standard. To the evacuated sweep side of the membrane reactor unit was added the following deaerated solution: 306.0 grams (3.64 moles) of hexene-1 and 23.0 grams of hexadecane. A mixture of hydrogen/carbon monoxide gas (51/49) was pressured to the reactor unit to approximately $7.58 \times 10^5$ N/m² (110 psi) and the contents were heated at 80°-85° C. for 69 hours. The catalyst side and sweep side were circulated at 400 cc/minute during this heating period.

Figure 3:
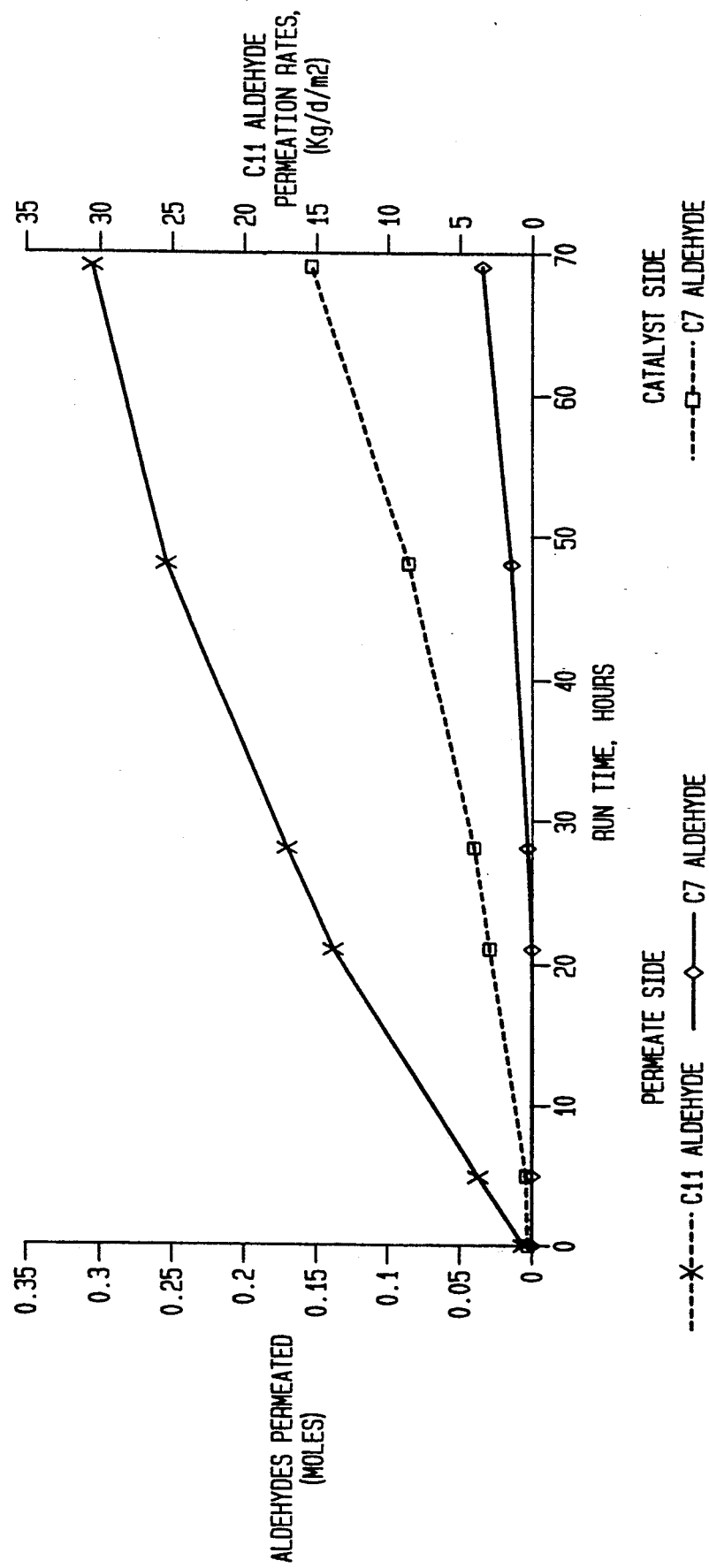
FIG. 3 is a graph comparing the effect which the perstraction sweep stream of hexene-1 has on the permeation rate of $C_{11}$ aldehydes formed from decene-1 feedstock.

Samples were withdrawn from both sides of the membrane separator periodically and the compositions analyzed by gas chromatography. The results are displayed in FIG. 3. At the conclusion of the run, the sweep side of the reactor was calculated to contain 52.17 grams of undecyl aldehyde which represents an overall permeation rate of the aldehyde of 17.8 kg/m²/day or 863 kg/μ/m²/day. The sweep side also contained 3.92 grams of heptyl aldehydes formed by the permeation of hexene-1 to the catalyst side of the separator. The final hexene-1 and undecyl aldehyde mixture on the sweep side was analyzed for rhodium and found to contain 0.23 ppm. This indicates that about 99.5% of the rhodium would be retained if all the undecyl aldehyde had permeated.

In a comparison run, decene-1 was hydroformylated as above and decene-1 was used as the sweep solvent. A crosslinked copolymer of isobutylene and p-bromomethyl styrene membrane was cast on Teflon ® and thereafter mounted in the membrane reactor unit between two 100 mesh stainless steel screens. The polymer thickness was 69.6 microns, with two 53.3 micron sheets of Teflon ® on the outer surface. To the evacuated catalyst side of the membrane reactor unit was added the organic reactor product which comprised 213 grams (1.24 mole) of undecyl aldehydes 14.54 grams of decene-1 (0.10 mole) and 14.42 grams of hexadecane as an internal standard. To the evacuated sweep side of the membrane reactor unit was added the following deaerated solution: 293.84 grams (2.10 moles) of decene-1 and 24.8 grams of hexadecane. A mixture of hydrogen/carbon monoxide gas (51/49) was pressured to the reactor unit to approximately $7.58 \times 10^5$ N/m² (110 psi) and the contents were heated at 80°-85° C. for 76 hours. The catalyst side and sweep side were circulated at 400 cc/minute during this heating period. Samples were withdrawn from both sides of the membrane separator periodically and the compositions analyzed by gas chromatography.

Figure 4:
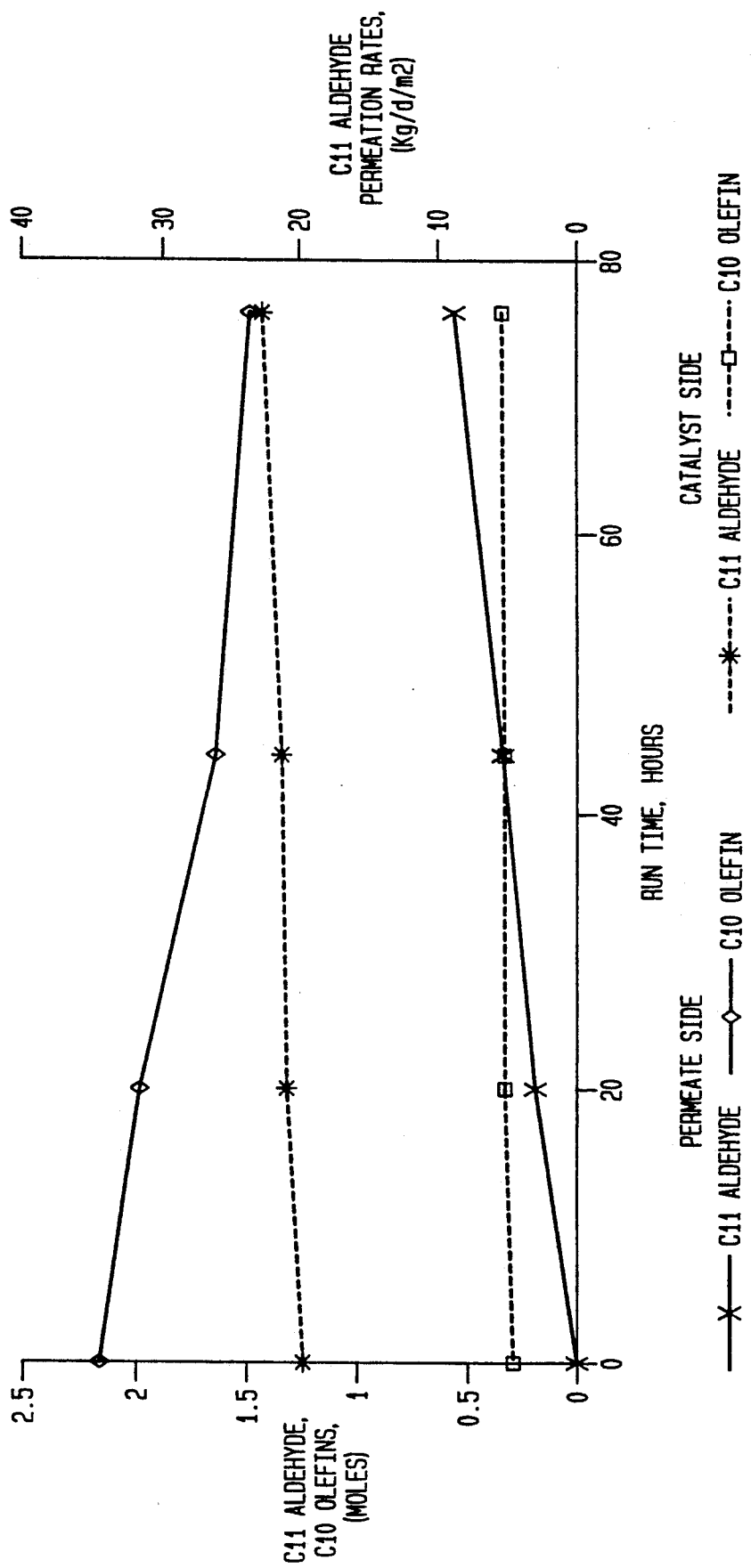
FIG. 4 is a graph comparing the effect which the perstraction sweep stream of decene-1 has on the permeation rate of $C_{11}$ aldehydes formed from decene-1 feedstock.

The results are displayed in FIG. 4. At the conclusion of the run, the sweep side of the reactor was calculated to contain 94.35 grams of undecyl aldehyde which represents an overall permeation rate of the aldehyde of 29.2 kg/m²/day or 2030 kg/μ/m²/day. The sweep side also contained 188 grams of decene-1. The catalyst side at the conclusion of the run contained, by analysis, 242 grams of undecyl aldehyde and 23 grams of decene-1. Thus, approximately 123.4 grams (0.72 mole) of undecyl aldehyde was produced during the separation experiment and 97.5 grams (0.70 mole) of decene-1 consumed. This result also demonstrates that the decene-1 that permeated the membrane to the side containing catalyst could be reacted and that the catalyst was still active. The final decene-1 and undecyl aldehyde mixture on the sweep side was analyzed for rhodium and found to contain 0.31 ppm. This indicated that about 99.6% of the rhodium would be retained if all the aldehyde initially charged had permeated.

EXAMPLE 2

In this experiment, the inventors demonstrated that feed olefin, e.g., decene-1, may be introduced into the sweep side of a membrane reactor, that the decene-1 permeates the membrane and is reacted on the catalyst side of the reactor, and that the product aldehyde permeates to the sweep side where it may be recovered from the original feed (i.e., decene-1) which is also the perstraction solvent. Further, the inventors have shown that the noble metal catalyst, in this case the rhodium, is substantially retained on the catalyst side by the membrane.

The aqueous catalyst solution was prepared in a nitrogen dry box. Into a 500 ml Erlenmeyer flask were weighed 210 grams of a 1N sodium bicarbonate solution, 3.78 grams (0.04494 mole) of sodium bicarbonate, and 4.8 grams ($1.567 \times 10^{-2}$ moles) of diphenyl phosphinobenzoic acid. The mixture was heated to about 75° C. with magnetic stirring to dissolve the diphenylphosphinobenzoic acid. Next, 6.0 grams ($2.995 \times 10^{-2}$ moles) of lauric acid were added to the mixture in the flask. The addition of the lauric acid should occur slowly to prevent foaming caused by the release of carbon dioxide. Once all the lauric acid dissolved, the mixture was cooled to about 50° C. and 0.45 grams ($1.744 \times 10^{-3}$ moles) of dicarbonyl acetyl acetonate rhodium were then added to the mixture. A hazy orange liquid resulted on stirring for approximately twenty minutes. The Erlenmeyer flask was stoppered and the catalyst solution removed from the nitrogen dry box for addition to the membrane reactor unit.

The crosslinked copolymer membrane was then mounted in the membrane reactor unit between two 100 mesh stainless steel screens. The polymer thickness was 48.5 microns, with two 53.3 micron sheets of Teflon ® on the outer surface. To the preheated evacuated catalyst side of the membrane reactor unit was added the entire 225 grams of the hazy orange liquid catalyst solution. To the evacuated sweep side of the membrane reactor unit was added the following deaerated solution: 300.0 grams (2.14 moles) of decene-1 and 23.0 grams of hexadecane. A mixture of hydrogen/carbon monoxide gas (51/49) was pressured to the reactor unit to approximately $7.58 \times 10^5$ N/m$^2$ (110 psi) and the contents were heated at 80°–85° C. for 145 hours. The catalyst side and sweep side were circulated at 400 cc/minute during this heating period. At 113 hours a sample was withdrawn from both sides of the membrane reactor and the compositions analyzed by gas chromatography.

The catalyst side of the reactor was calculated to contain 57.4 grams (0.338 moles) of aldehyde and 17.6 grams (0.114 moles) of decene-1. The sweep side of the reactor was calculated to contain 49.6 grams (0.292 moles) of aldehyde and 184.6 grams (1.191 moles) of decene-1. Thus, approximately 33% of the decene-1 was converted to undecyl aldehyde. The combined reaction and permeation rate of the aldehyde was 10.3 kg/m$^2$/day. The final decene-1 and undecyl aldehyde mixture on the sweep side was analyzed for rhodium and found to contain 1.33 ppm. The original starting rhodium concentration was 798 ppm on the catalyst side.

EXAMPLE 3

The present inventors have also conducted two comparative demonstration runs to illustrate that the olefinic feedstock can be successfully used as the perstraction sweep solvent during membrane separation of hydroformylation reaction products and unreacted olefins from a noble metal catalyst without substantially reducing the rate of permeation of the hydroformylation reaction products through the membrane. These examples also demonstrate that the diffusion of the sweep solvent through the membrane to the retentate side of the membrane does not result in the contamination of the crude reaction products but does provide an effective source of feed for reaction with the catalyst to desired reaction products. In these comparative runs, the ligand is completely soluble in the organic reaction medium.

Figure 5:
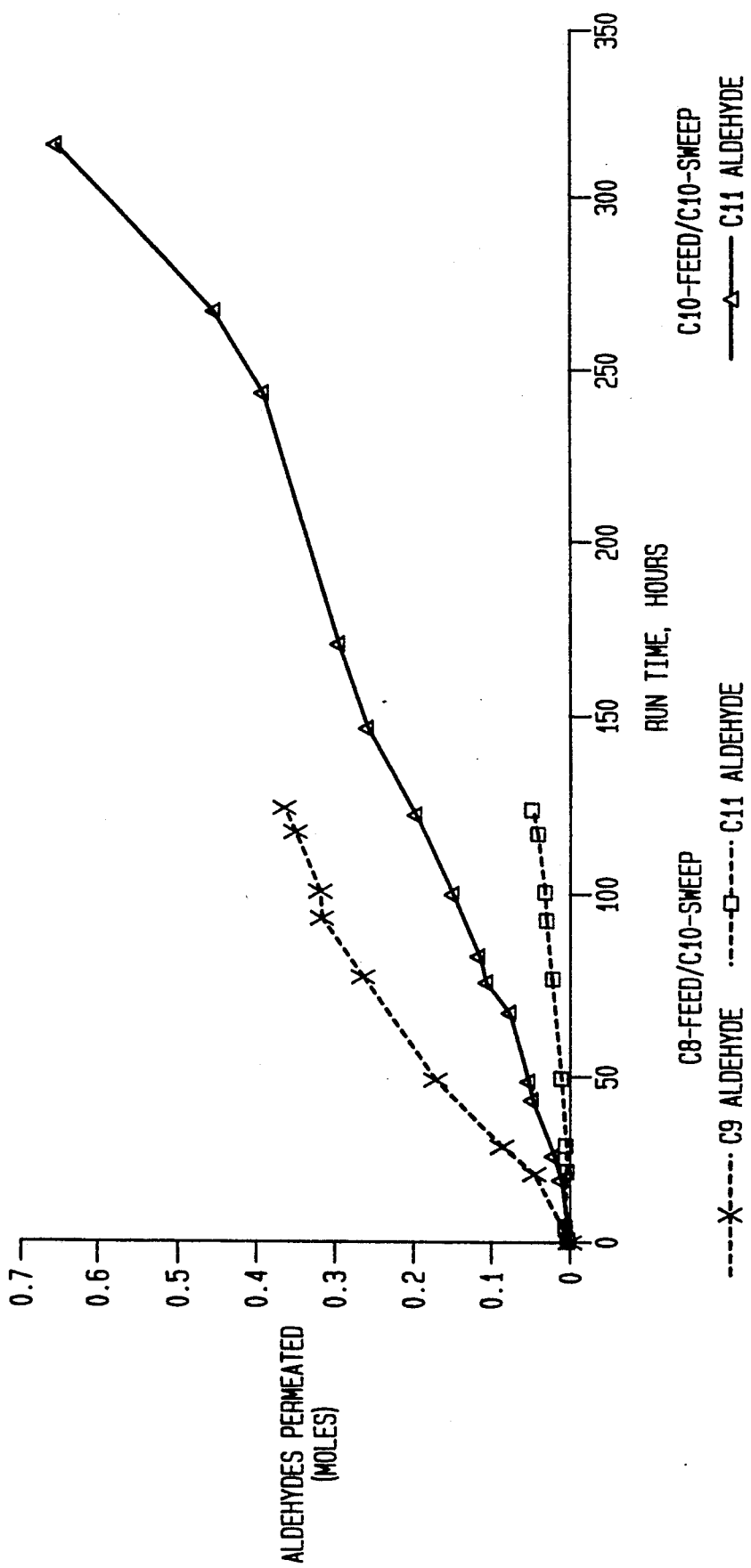
FIG. 5 is a graph comparing the effect which the perstraction sweep stream of decene-1 have on the permeation rates of $C_9$ and $C_{11}$ aldehydes formed from octene-1 and decene-1 feedstock, respectively.

As illustrated in FIG. 5, decene-1 was hydroformylated using a rhodium catalyst and trioctylphosphine as a ligand on the retentate side of a polyethylene succinate membrane. Decene-1 was also used as a sweep solvent on the permeate side of the membrane and the product aldehyde (i.e., a $C_{11}$ aldehyde) was allowed to permeate in a perstraction mode under the same pressure and temperature as the retentate side of the membrane. The rate of aldehyde permeation when the feed olefin was used as the perstraction sweep stream was approximately 3.0 kg/m$^2$/day.

This rate of permeation was only slightly less than the rate demonstrated when the hydroformylation feed was octene-1, the sweep stream was decene-1 and the membrane was a polyureaurethane membrane. The octene-1/decene-1 experiment resulted in a rate of permeation of $C_9$ aldehydes in the amount of 4.6 kg/m$^2$/day. When octene-1 was used as the hydroformylation feed and decene-1 as the sweep stream for perstraction no significant reaction took place on the permeate side of the membrane, indicating that no rhodium permeated together with the aldehydes. The fact that some of the sweep diffuses through to the retentate side of the membrane and reacts with the rhodium catalyst is demonstrated by the small amount of $C_{11}$ aldehydes detected in the permeate.

The similarity in aldehyde permeation rates between the two feed/sweep systems, i.e., (decene-1/decene-1) and (octene-1/decene-1), illustrates that the reaction of the decene-1 to undecanals occurred substantially on the retentate side of the membrane and not by reaction of the decene-1 with rhodium that may have permeated to the permeate side of the membrane. Likewise, since it has been demonstrated that virtually no rhodium passed through the membrane, it can be concluded that the undecanal permeated through the membrane and did not pass due to mechanical or other failure. Accordingly, when decene-1 is used as both the reaction feed and perstraction sweep solvent, it was able to effectively perstract the hydroformylation product, i.e., the undecanals, from the reaction mixture.

While we have shown and described several embodiments in accordance with our invention, it is to be clearly understood that the same are susceptible to numerous changes apparent to one skilled in the art. Therefore, we do not wish to be limited to the details shown and described but intend to show all changes and modifications which come within the scope of the appended claims.

What is claimed is:

1. A method for separating a noble metal catalyst from a crude reaction product of a noble metal-catalyzed hydroformylation reaction by means of perstraction, said crude reaction product including a Group VIII noble metal-ligand complex catalyst, unreacted olefin feed and hydroformylation reaction product, which comprises: (a) contacting said crude reaction product under perstraction conditions with a membrane capable of allowing a substantial portion of said unreacted olefin feed and hydroformylation reaction product to pass therethrough as permeate while retaining a substantial portion of said Group VIII noble metal-ligand complex catalyst as retentate; (b) removing said permeate by sweeping it away from said membrane by means of a sweep stream which is the same as said olefin feed used in the hydroformylation reaction; and (c) retaining said Group VIII noble metal-ligand complex catalyst as retentate.

2. The method according to claim 1 wherein said noble metal-catalyzed hydroformylation reaction includes the steps of: reacting said olefin feed with hydrogen and carbon monoxide in the presence of a Group VIII noble metal-ligand complex catalyst, at a temperature in the range between about 80° to 125° C. to produce an aldehyde having a normal to iso ratio in the range between about 0.5:1 to about 80:1.

3. The method according to claim 1 wherein said ligand is an alkylated or arylated ligand.

4. The method according to claim 3 wherein said alkylated or arylated ligand is a phosphine ligand with at least one alkyl group bonded thereto.

5. The method according to claim 4 wherein said phosphine ligand is triphenyl phosphine.

6. The method according to claim 5 wherein the aryl group is alkylated and said alkyl group comprises between about 2 to about 8 carbons.

7. The method according to claim 6 wherein said alkyl group is bonded to the para position about said triphenyl phosphine.

8. The method according to claim 1 wherein the Group VIII noble metal is rhodium.

9. The method according to claim 1 wherein said membrane is a dense, nonpolar polymeric membrane selected from the group consisting of: polypropylene membranes, low density polyethylene crosslinked membranes, and high density polyethylene crosslinked membranes.

10. The method according to claim 1 wherein said retentate retains at least about 99% of said Group VIII noble metal-ligand complex catalyst.

11. The method according to claim 1 wherein said olefin feed is a $C_4$–$C_{20}$ olefin.

12. The method according to claim 11 wherein said olefin feed and said sweep stream are both decene-1.

13. The method according to claim 1 wherein said sweep stream permeates through to the retentate side of said membrane so as to constitute both said sweep stream and said olefin feed.

14. A method for producing higher aldehydes and higher alcohols which comprises:
(a) hydroformylating an olefin feed with synthesis gas in the presence of a Group VIII noble metal-ligand complex catalyst to form a crude reaction product comprised of unreacted olefin feed, hydroformylation reaction product and a Group VIII noble metal-ligand complex catalyst;
(b) removing said Group VIII noble metal-ligand complex catalyst from said crude reaction product by feeding said crude reaction product under perstraction conditions to a membrane separator which comprises a membrane capable of allowing a substantial portion of said hydroformylation reaction product and olefin feed to pass therethrough as permeate while retaining a substantial portion of said Group VIII noble metal-ligand complex catalyst as permeate;
(c) recovering said permeate by sweeping it away from said membrane by means of a sweep stream which is the same as said olefin feed used in the hydroformylation reaction;
(d) retaining said Group VIII noble metal-ligand complex catalyst as retentate; and
(e) recycling the retained Group VIII noble metal-ligand complex catalyst to said hydroformylation step (a).

15. The method according to claim 14 wherein said sweep stream permeates through the retentate side of said membrane so as to act as both said sweep stream and said olefin feed.

16. The method according to claim 14 wherein said noble metal catalyzed hydroformylation reaction includes the steps of: reacting said olefin feed with hydrogen and carbon monoxide in the presence of a Group VIII noble metal-ligand complex catalyst, at a temperature in the range between about 80° to 125° C., to produce an aldehyde having a normal to iso ratio in the range between about 0.5:1 to about 80:1.

17. The method according to claim 14 wherein said ligand is an alkylated or arylated ligand.

18. The method according to claim 17 wherein said alkylated or arylated ligand is a phosphine ligand with at least one alkyl group bonded thereto.

19. The method according to claim 18 wherein said phosphine ligand is triphenyl phosphine.

20. The method according to claim 19 wherein the aryl group is alkylated and said alkyl group comprises between about 2 to about 8 carbons.

21. The method according to claim 20 wherein said alkyl group is bonded to the para position about said triphenyl phosphine.

22. The method according to claim 14 wherein the Group VIII noble metal is rhodium.

23. The method according to claim 14 wherein said membrane is a dense, nonpolar polymeric membrane selected from the group consisting of: polypropylene membranes, low density polyethylene crosslinked membranes, and high density polyethylene crosslinked membranes.

24. The method according to claim 14 wherein said retentate retains at least about 99% of said Group VIII noble metal-ligand complex catalyst.

25. The method according to claim 14 wherein said olefin feed is a $C_4$–$C_{20}$ olefin.

26. The method according to claim 25 wherein said olefin feed and said sweep stream are both decene-1.

27. A method for separating reaction products from reactants in a membrane reactor which comprises a retentate compartment and a permeate compartment divided by mean of a membrane, wherein the separation occurs under perstraction conditions and the sweep stream which passes through said permeate compartment is the same as said reactants used to form the reaction products.

28. A method for separating a water-soluble noble metal catalyst from a crude reaction product of a noble metal-catalyzed hydroformylation reaction run in aqueous solution, in an aqueous emulsion or as an aqueous suspension, said crude reaction product including an aqueous phase containing a water-soluble Group VIII noble metal-ligand complex catalyst and an organic phase containing unreacted olefin feed and an organic hydroformylation reaction product, which comprises: (a) contacting said crude reaction product under perstraction conditions with a hydrophobic membrane capable of allowing a substantial portion of said unreacted olefin feed and said organic hydroformylation reaction product to pass therethrough as permeate while retaining a substantial portion of said water-soluble Group VIII noble metal-ligand complex catalyst as retentate; (b) removing said permeate by sweeping it away from said membrane by means of a sweep stream which is the same as said olefin feed used in the hydroformylation reaction; and (c) retaining said water-soluble Group VIII noble metal-ligand complex catalyst as retentate.

29. The method according to claim 28 wherein said noble metal-catalyzed hydroformylation reaction includes the steps of: reacting said olefin feed with hydrogen and carbon monoxide in the presence of a Group VIII noble metal-ligand complex catalyst, at a temperature in the range between about 80° to 125° C. to produce an aldehyde having a normal to iso ratio in the range between about 0.5:1 to about 80:1.

30. The method according to claim 29 wherein said ligand is one compound selected from the group consisting of: Na-p-(diphenylphosphino)benzoate, Na-p-(diphenylphosphino) benzenesulfonate, Na-m-(diphenylphosphino)benzenesulfonate, and tris-(sodium m-sulfophenyl)-phosphine.

31. The method according to claim 28 wherein said water-soluble Group VIII noble metal is rhodium.

32. The method according to claim 29 further comprising adding a surfactant to said noble metal-catalyzed hydroformylation reaction.

33. The method according to claim 32 wherein said surfactant is one compound selected from the group consisting of: cetyltrimethylammonium bromide, sodium laurate, sodium stearate, Na-p-toluenesulfonic acid, and linear dodecylbenzene sulfonate.

34. The method according to claim 28 wherein said hydrophobic membrane is selected from the group consisting of: high density polyethylene crosslinked membranes, natural latex rubber membranes, polyvinylidene difluoride membranes, polychlorotrifluoroethylene membranes, polytetrafluoroethylene membranes, crosslinked bromobutyl rubber membranes, and crosslinked copolymer membranes of isobutylene and p-bromomethyl styrene.

35. The method according to claim 28 wherein said retentate retains at least about 99% of said water-soluble Group VIII noble metal-ligand complex catalyst.

36. The method according to claim 28 wherein said olefin feed is a $C_4$–$C_{20}$ olefin.

37. The method according to claim 36 wherein said olefin feed and said sweep stream are both decene-1.

38. The method according to claim 28 wherein said sweep stream permeates through to the retentate side of said membrane so as to constitute both said sweep stream and said olefin feed.

39. A method for producing higher aldehydes and higher alcohols which comprises:
  (a) hydroformylating an olefin feed with synthesis gas in the presence of a water-soluble Group VIII noble metal-ligand complex catalyst to form a crude reaction product comprised of an organic phase containing unreacted olefin feed and organic hydroformylation reaction product and an aqueous phase containing a water-soluble Group VIII noble metal-ligand complex catalyst;
  (b) removing said water-soluble Group VIII noble metal-ligand complex catalyst from said crude reaction product by feeding said crude reaction product under perstraction conditions to a membrane separator which comprises a hydrophobic membrane capable of allowing a substantial portion of said hydroformylation reaction product and olefin feed to pass therethrough as permeate while retaining a substantial portion of said water-soluble Group VIII noble metal-ligand complex catalyst as permeate;
  (c) recovering said permeate by sweeping it away from said membrane by means of a sweep stream which is the same as said olefin feed used in the hydroformylation reaction;
  (d) retaining said Group VIII noble metal-ligand complex catalyst as retentate; and
  (e) recycling the retained water-soluble Group VIII noble metal-ligand complex catalyst to said hydroformylation step (a).

40. The method according to claim 39 wherein said sweep stream permeates through the retentate side of said membrane so as to act as both said sweep stream and said olefin feed.

41. The method according to claim 39 wherein said noble metal catalyzed hydroformylation reaction includes the steps of: reacting said olefin feed with hydrogen and carbon monoxide in the presence of a water-soluble Group VIII noble metal-ligand complex catalyst, at a temperature in the range between about 80° to 125° C., to produce an aldehyde having a normal to iso ratio in the range between about 0.5:1 to about 80:1.

42. The method according to claim 39 wherein said water-soluble ligand is one compound selected from the group consisting of: Na-p-(diphenylphosphino)benzoate, Na-p-(diphenylphosphino) benzenesulfonate, Na-m-(diphenylphosphino)benzenesulfonate, and tris-(sodium m-sulfophenyl)-phosphine.

43. The method according to claim 39 wherein said water-soluble noble metal catalyst is rhodium.

44. The method according to claim 39 further comprising adding a surfactant to said noble metal catalyzed hydroformylation reaction.

45. The method according to claim 44 wherein said surfactant is one compound selected from the group consisting of: cetyltrimethylammonium bromide, sodium laurate, sodium stearate, Na-p-toluenesulfonic acid, and linear dodecylbenzene sulfonate.

46. The method according to claim 39 wherein said membranes is selected from the group consisting of: high density polyethylene crosslinked membranes, natural latex rubber membranes, a polyvinylidene difluoride membranes, polychlorotrifluoroethylene membranes, polytetrafluoroethylene membranes, crosslinked bromobutyl rubber membranes, and crosslinked copolymer membranes of isobutylene and p-bromomethyl styrene.

47. The method according to claim 39 wherein said retentate retains at least about 99% of said water-soluble noble metal catalyst.

48. The method according to claim 39 wherein said olefin feed is a $C_4$–$C_{20}$ olefin.

49. The method according to claim 48 wherein both said olefin feed and said sweep stream are decene-1.

* * * * *